Figure 2:
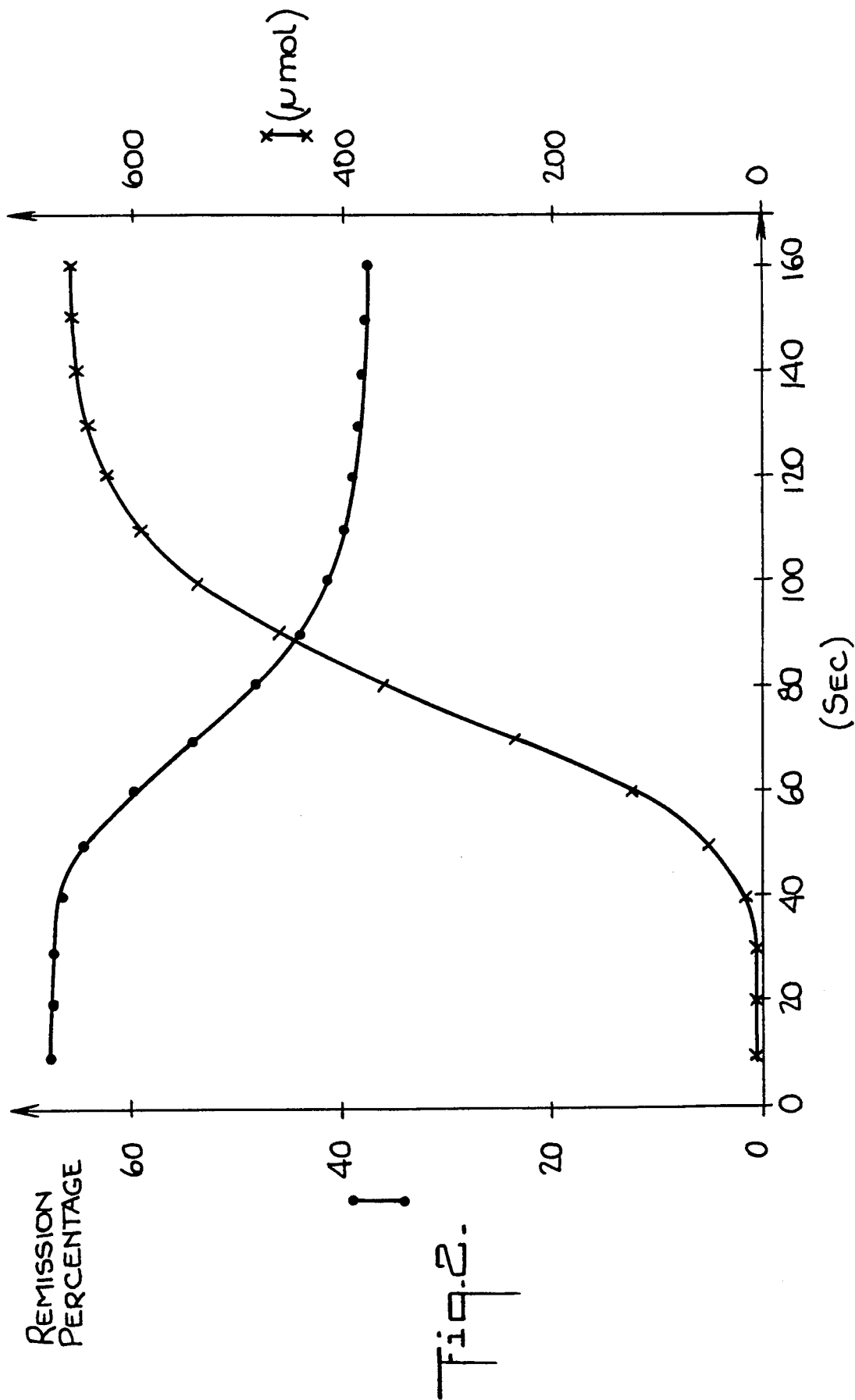

United States Patent [19]

Bartl et al.

[11] Patent Number: 5,059,525
[45] Date of Patent: * Oct. 22, 1991

[54] DRY REAGENT FOR BLOOD COAGULATION TESTS

[75] Inventors: Knut Bartl, Wilzhofen; Udo Becker, Marburg; Helmut Lill, Wielenbach; Hans Wielinger, Weinheim, all of Fed. Rep. of Germany

[73] Assignee: Boehringer Mannheim GmbH, Mannheim, Fed. Rep. of Germany

[*] Notice: The portion of the term of this patent subsequent to Nov. 22, 2005 has been disclaimed.

[21] Appl. No.: 530,469

[22] Filed: May 29, 1990

Related U.S. Application Data

[63] Continuation of Ser. No. 798,955, Nov. 18, 1985, abandoned.

[30] Foreign Application Priority Data

Nov. 19, 1984 [DE] Fed. Rep. of Germany ....... 3442271
May 8, 1985 [DE] Fed. Rep. of Germany ....... 3516579

[51] Int. Cl.$^5$ ............................................. C12Q 1/56
[52] U.S. Cl. ...................................... 435/13; 435/176; 435/177; 435/212; 435/214; 435/217; 435/805; 436/69; 436/169; 436/170; 436/810; 422/56; 422/57; 530/802
[58] Field of Search ................. 435/13, 176, 177, 805, 435/212, 214, 217; 436/69, 166, 169, 170, 810; 530/802; 422/56, 57

[56] References Cited

U.S. PATENT DOCUMENTS

| | | | |
|---|---|---|---|
| 4,042,335 | 8/1977 | Clement | 422/56 X |
| 4,473,639 | 9/1984 | Summer et al. | 435/13 |
| 4,557,901 | 12/1985 | Koyama et al. | 422/56 |
| 4,755,461 | 7/1988 | Lawson et al. | 435/13 |
| 4,786,603 | 11/1988 | Wielinger et al. | 436/69 |
| 4,788,152 | 11/1988 | Doeding et al. | 436/69 |

FOREIGN PATENT DOCUMENTS 103247 3/1984 European Pat. Off. .
111831 6/1984 European Pat. Off. .

OTHER PUBLICATIONS

Palmer et al., "Cold-Induced Contact Surface Activation of the Prothrombin Time in Whole Blood", *Blood*, vol. 59, No. 1, (Jan. 1982), pp. 38–42.
Triplett, D. in Clinical Laboratory Annual, vol. 1 (1982): 243–287.
Sigma Chemical Company Catalogue, Feb. 1984, pp. 197–200, 1010, 1027–1029, 1031, 1032, 1047, 1078.
Walter (1983) Analytical Chemistry, vol. 55, No. 4, pp. 498–514.
Clark (1984) Staining Procedures, 4th ed., Waverly Press, Inc., Baltimore, MD., pp. 203 and 233.
Fareed et al. (1983), Clinical Chemistry, vol. 29, No. 2, pp. 225–236.
Fareed et al., (1983), Clinical Chemistry, vol. 29, No. 9, pp. 1641–1658.

*Primary Examiner*—Esther L. Kepplinger
*Assistant Examiner*—Carol A. Spiegel
*Attorney, Agent, or Firm*—Felfe & Lynch

[57] ABSTRACT

The present invention provides a dry reagent for blood coagulation tests in which an at least partial course of the coagulation cascade takes place, comprising a carrier material which contains a chromophoric substrate of a protease of the blood coagulation system, at least one factor and/or co-factor of the blood coagulation system and a buffer.

19 Claims, 3 Drawing Sheets

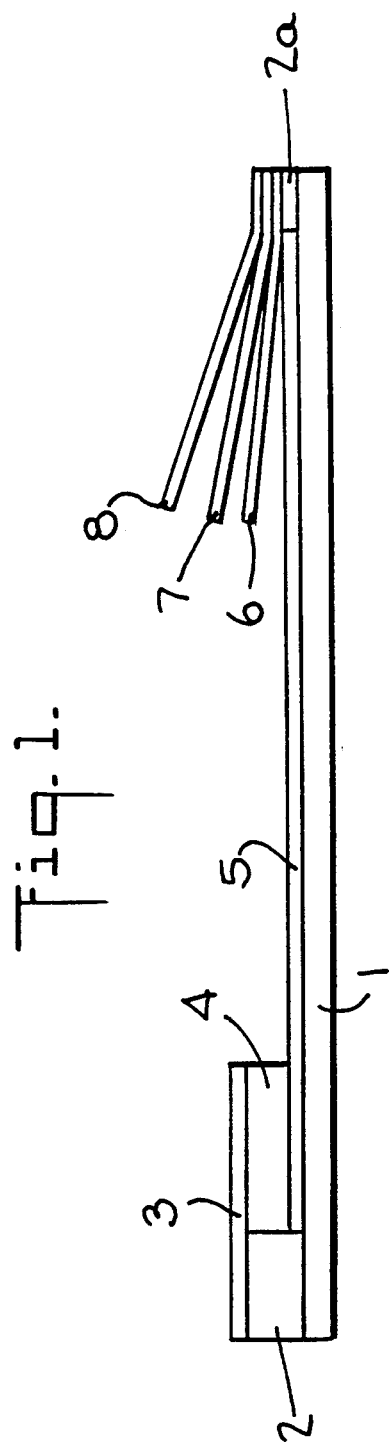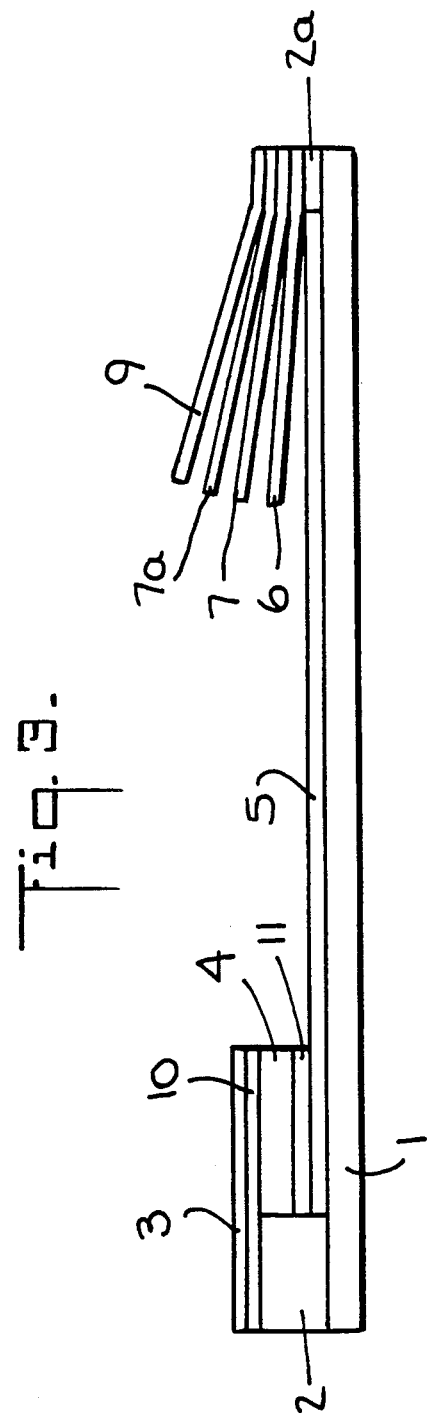

DRY REAGENT FOR BLOOD COAGULATION TESTS

This application is a continuation, of application Ser. No. 798,955, filed Nov. 18, 1985, now abandoned.

The present invention provides a dry reagent for blood coagulation tests.

For clinical diagnosis, therapy and prophylaxis, methods for the determination of the blood coagulation system, especially so far as it concerns the functionability of this system and the discovery of deficiencies thereof possibly present, have already achieved a great importance which, however, is continuously increasing. Consequently, the need for simple methods for such coagulation tests which can be carried out without great expense has also increased.

Amongst the methods for the determination of clinically relevant chemical parameters, the determination methods carried out on test strips have achieved wide use since, as a rule, they permit a rapid determination to be carried out without any or with only small expense for apparatus. In the meantime, such test strip methods have reached a high degree of exactitude and, therefore, also permit quantitative determinations to be carried out with great dependability.

Hitherto, however, it has not been possible also to use such test strip methods for the determination of the blood coagulation system. The coagulation system is a multifactor system which is extraordinarily difficult to define exactly. Furthermore, the coagulation cascade is very strongly influenced by surface forces, as is described, for example, in British Medical Bulletin, 34, 107–112/1978 and in Blood, 59, 38–42/1982. In addition, every plasma contains thrombocytes which are activated by solid surfaces and, in an activated state, in turn further influence the coagulation cascade and thereby falsify it.

Surprisingly, we have now found that it also is possible to carry out blood coagulation tests on test strips in which the coagulation cascade takes place at least partly.

Thus, according to the present invention, there is provided a dry reagent for blood coagulation tests in which an at least partial course of the coagulation cascade takes place, comprising a chromophoric substrate of a protease of the blood coagulating system, at least one factor and/or cofactor of the blood coagulation system and a buffer substance.

The evaluation of the test strips according to the present invention can take place by all methods known for this purpose, for example with the help of a comparative color scale. However, because of the higher exactitude, remission photometry is preferred. When using remission photometry, apart from an end point measurement, a kinetic measurement can also be carried out. The tests can also be carried out with and without pre-incubation.

The dry reagent according to the present invention can be used, depending upon the particular composition thereof, for carrying out Quick tests and PTT tests (partial thromboplastin time) and for determinations of prothrombin, Factor X, Factor VIII, Factor VII and Factor IX.

If the dry reagent according to the present invention is used for carrying out the Quick test, then it contains thromboplastin, a chromophoric thrombin substrate and $Ca^{2+}$-ions.

If the dry reagent according to the present invention is used for the determination of prothrombin, then it contains chromophoric thrombin substrate, FactorXa and, as cofactors, Factor V, $Ca^{2+}$ and phospholipid.

If the dry reagent according to the present invention is used for the determination of Factor X, then it contains the venom of Russell's viper (RVV) or the pure or partly purified Factor X activator from this venom, $Ca^{2+}$ and a chromophoric Factor Xa substrate.

If the dry reagent according to the present invention is used for the determination of Factor VIII, then it contains Factor IXa, as well as traces of thrombin, $Ca^{2+}$, phospholipid and a chromophoric Factor Xa substrate. Instead of the Factor Xa substrate, it is also possible to use a chromophoric thrombin substrate.

If the dry reagent according to the present invention is used for the determination of Factor VII, then it contains thromboplastin, $Ca^{2+}$ and a chromophoric Factor Xa substrate.

If the dry reagent according to the present invention is used for the determination of Factor IX, then it contains activated contact factors with a sufficient content of Factor XIa or a Factor XIa, $Ca^{2+}$ and chromophoric Factor IXa substrate. Instead of a Factor IXa substrate, the reagent can additionally contain phospholipid, Factor VIII, traces of thrombin and a chromophoric Factor Xa substrate.

For carrying out the PTT test, the reagent according to the present invention contains partial thromboplastin, contact activators, a chromophoric thrombin substrate, phospholipid and $Ca^{2+}$, the contact activator preferably being ellagic acid.

The dry reagent according to the present invention can, in principle, consist of a single carrier material (reaction: matrix) which contains substrate, blood coagulation factor or co-factor and buffer substance. However, the dry reagent preferably also contains a second carrier material with an oxidation agent (oxidation matrix). In this case, the first carrier material contains an aniline or phenol derivative forming a color with the chromophore of the chromophoric substrate in the presence of the oxidation agent of the second carrier material.

In principle, the dry reagent according to the present invention can contain any desired chromophoric substrate of a protease of the blood coagulation system, with the proviso that this substrate does not change the course of the coagulation cascade in the presence of the carrier material. As chromophoric substrates in the scope of the present invention, there have proved to be well suited compounds of the general formula :

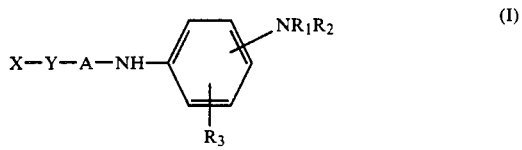

in which A is the amino acid arginine or lysine, X is an N-terminal amino acid protective group, Y is a single bond or a chain of 1 to 3 amino acids, $NR_1R_2$ is a group in the o or p-position in which $R_1$ and $R_2$, independently of one another, are hydrogen atoms or alkyl radicals containing up to 3 carbon atoms or a nitro group and $R_3$ is a hydrogen atom, a carboxylic ester or carboxylamido group, a halogen atom, a nitro group or an alkyl radical containing up to 3 carbon atoms.

A chromophoric substrate in which X-Y-A represents Tos-Gly-Pro-Arg is especially preferred in the scope of the present invention.

As color-forming aniline or phenol derivative, there can be used the compounds known for this purpose, N-methylanthranilic acid, dimethylanthranilic acid, N-ethyl-N-(3'-sulphobenzene)-aniline and 2,3-xylenol being preferred.

In the case of the preferred embodiment of the present invention, which contains a second absorbent carrier material impregnated with an oxidation agent (oxidation matrix), the first absorbent carrier material (reaction matrix) is preferably impregnated with Tos-Gly-Pro-Arg-p-phenylenediamine as chromophoric substrate and N-methylanthranilic acid as color-forming aniline derivative and the second absorbent material contains potassium ferricyanide as oxidation agent.

The reagent according to the present invention can be used for determination with plasma or with whole blood. If the determination is carried out with whole blood, it is preferable additionally to provide a third absorbent carrier material (application matrix) on to which the blood sample is applied. Furthermore, at least one fibre fleece is preferably also provided which is arranged between the third and the first carrier material and serves as a separation and transport matrix. Such a fibre fleece serving as separation or transport matrix can also be provided between the first and second carrier material. For the construction and operation of such tests, reference is made to Federal Republic of Germany Patent Specification No. 30 29 579.5.

As carrier material for the reaction matrix, there can, in the scope of the present invention, be used an absorbent, swellable or soluble film-forming carrier material, for example a carrier material known for test strips, such as paper and similar fleece materials, for example tea bag paper and the like.

As carrier materials for the reaction matrix, there can also be used swellable substances, for example gelatine or cellulose films, which, by the incorporation of pigments, can be made more permeable. However, the carrier material can also consist of a water-soluble, film-forming polymer into which the reagents are incorporated and which dissolves wholly or partly in the substrate solution so that the reagents are able to act. As described hereinafter, the reagentcontaining film is applied either to a base film or on to the surface of the separation or transport matrix or the second carrier material.

These polymers must be soluble in water at temperatures of 20 to 50° C. and it must be possible to produce films from them which are water-swellable or water-soluble. As polymers, there can be used, for example, cellulose derivatives, such as methyl celluloses, methylhydroxyethyl celluloses, hydroxyethylmethyl celluloses, as well as partly and fully saponified polyvinyl acetates, polyvinylpyrrolidones, polyethylene oxides, gelatines, polyxanthanes, polyacrylamides and the like.

As carrier materials for the oxidation matrix, there can be used those known for test strips, such as paper, glass and synthetic resin fleeces, meshes and fabrics of fibre material or absorbent, porous films or gels. As fibre fleeces serving as separation and transport matrix, there are preferably used those consisting of an inert, non-absorbent fibre material, preferably of glass fibres, synthetic resin fibres or other synthetic or natural mineral fibres.

Furthermore, the reagent according to the present invention can also contain a base film and/or a covering film, which is preferably transparent, as well as optionally one or more distance pieces. Such base and covering films and distance pieces are described, for example, in Federal Republic of Germany Patent Specification No. 30 29 579.

The production of the reagent according to the present invention takes place in such a manner that an impregnation solution of appropriate composition is first prepared and the absorbent carrier material then impregnated therewith and dried. Apart from the components already mentioned above, the impregnation solutions contain, as a rule, additional buffer substances of appropriate pH value, Tris buffer and GOOD buffer having proved to be especially useful. The dried impregnated carrier material is then cut up into the desired format and finally optionally assembled with the further components mentioned above.

For the production of dry reagents from soluble film formers, solutions are prepared from the polymers which are so viscous that films can be produced from them by known production processes, such as raking, forehand processes, roll coating and the like, the reagents, buffer substances, adjuvants and reagent stabilisers then being incorporated into these solutions. The coating masses are applied to carrier films, dried, optionally assembled with further above-mentioned components and the finished films worked up to give test strips.

Figure 4:
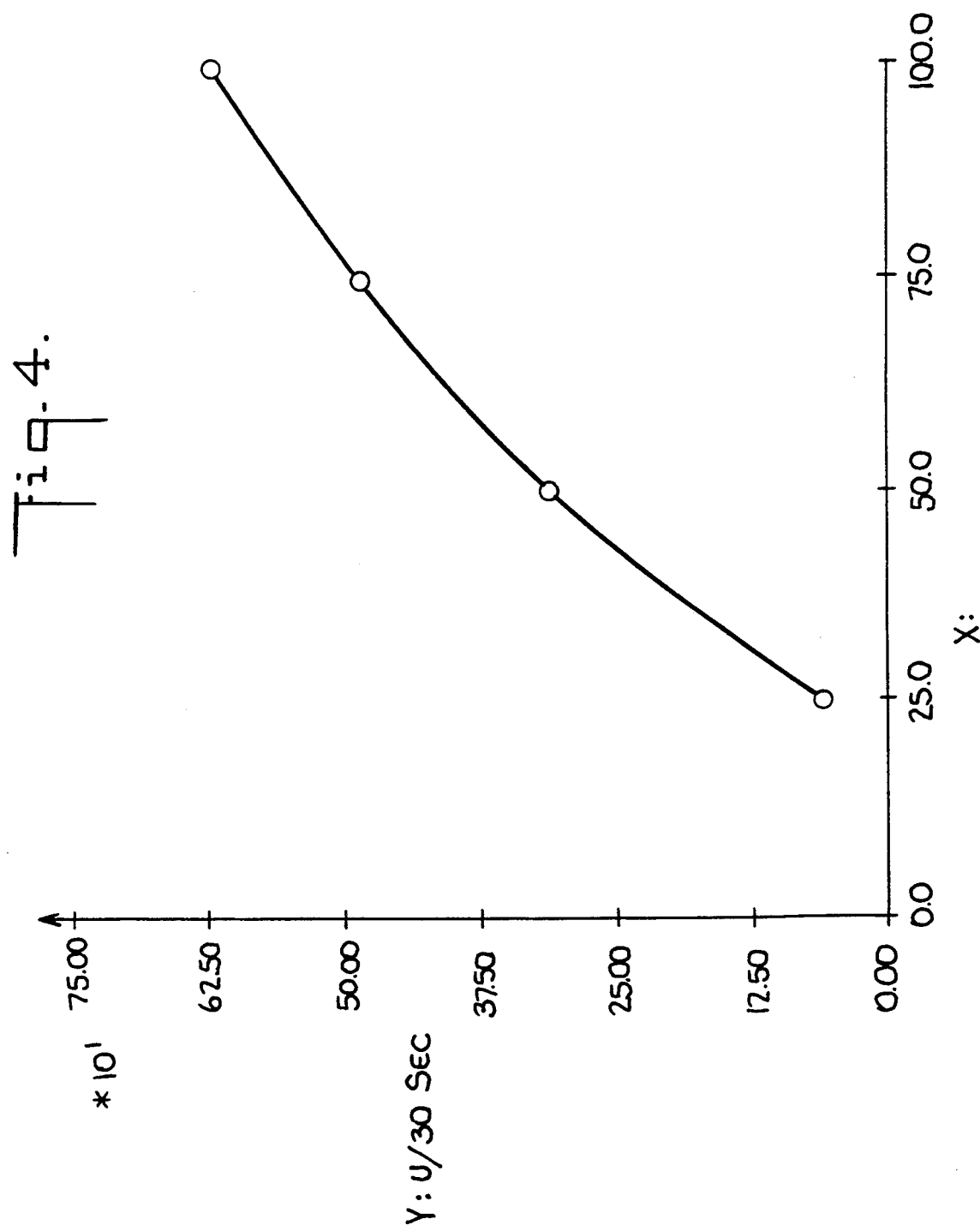

The following Examples are given for the purpose of illustrating the present invention, reference being made to the accompanying drawings, in which: FIG. 1 is a test strip according to the present invention for the determination of the Quick time, with the use of whole blood, FIG. 2 is a remission curve produced with the use of the test strip according to FIG. 1, FIG. 3 is another embodiment of the test strip according to the present invention for the determination of prothrombin in whole blood, and FIG. 4 is a calibration curve for prothrombin determination with the test strips of FIG. 3.

Example 1

Production of a test strip for the determination of the Quick time from blood or plasma For the production of a test strip, 2 papers are impregnated:

A. Reagent and substrate paper

A solution is prepared of the following composition:

| | |
|---|---|
| Tris-HCl | 0.025 mol/l. (buffer) |
| Tos—Gly—Pro—Arg-p-phenylene diamine | 0.001 mol/l. (substrate) |
| N-methylanthranilic acid, calcium salt | 0.03 mol/l. (reagent) |

A filling of commercially available thromboplastin a is reconstituted with .8 ml. of this solution and a paper of appropriate thickness and absorbency, for example tea bag paper of 12 g./m$^2$ per unit area, 0.05 mm. thickness and 50 ml. per m$^2$ absorbency volume, is impregnated therewith. The paper is then dried at 30° C. in the air and cut into 1 cm. wide strips.

B. Oxidation paper

A similar paper is impregnated with a solution of potassium ferricyanide (0.015 mol/l.) and cut up into a width of 6 mm. The material is worked up to give test strips, such as are described in Federal Republic of Germany Patent Specification No.31 30 749, the construction thereof being shown in FIG. 1, in which 1 carrier film
2 and 3a distance blocks
3 application matrix
4 glass fibre fleece (separation fleece)
5 glass fibre fleece (transport fleece)
6 oxidation paper
7 reagent and substrate paper
8 transparent covering film.

If 30 μl. citrate blood are applied to the application matrix 3, then, within 30 to 60 seconds, the plasma part penetrates the whole of the glass fibre fleeces 4 and 5, whereas the arythrocytes are held back. By applying pressure to the transparent covering film, the plasma now comes into contact with the reagent paper and the oxidation paper, which are uniformly moistened. Depending upon the activity of the plasma, a blue coloration is formed, the point of time of the appearance of which represents a measure of the Quick time of the sample. The time which transpires from the application of pressure to the transparent covering film up to the formation of the blue colored material is thus a measure for the Quick value of the sample. The appearance of the blue colour signal is measured in a remission spectrometer at a wavelength of 565 to 850 nm. For the recognition of the point or time, it is preferable to choose a predetermined remission change, for example a 1 or 2% remission decrease, or reference is made to a predetermined amount of split substrate.

Example 2

On to a test strip according to Example 1 are applied 30 μl. of citrate plasma and, after pressing on the reagent and substrate paper, the remission is measured in dependence upon the time. There is obtained the remission curve illustrated in FIG. 2. By recalculation of remission % into the corresponding concentration of split substrate, there is obtained the chronological course of the substrate splitting. If, for the reading off of the reaction time, there is used a remission change of 2% in comparison with the starting value, then, according to FIG. 2, there is obtained a time of 45 seconds. This corresponds to an amount of substrate of 30 μmol, i.e. 4.5% of the total amount of substrate present.

Example 3

On to test strips according to Example 1 is alternatingly successively applied citrate blood or citrate plasma of the same donor. If the reaction time is calculated according to Example 2, there is given, from several experiments, on average, for plasma 43.2 seconds and for blood of 44.3 seconds which, in the case of the variation coefficient of 7.7% determined for the method, is not significantly different from one another.

Example 4

A normal plasma pool from 10 donors, prepared according to German Industrial Standard DIN 58939, is diluted stepwise with physiological sodium chloride solution. If the undiluted plasma corresponds to a Quick value of 100% of the norm, then the 1:2 dilution corresponds to 50% and the 1:4 dilution to 25% of the norm. The samples are applied to test strips which have been produced according to Example 1 and the reaction time determined according to Example 2. The reaction times are plotted against the reciprocal plasma dilutions. There is obtained a line, the measurement points of which correlate according to linear regression with r = 0.999. This means that the criterion for the calibration of the Quick test with a normal pool plasma is provided since, between the activity of the sample and the reaction time, a hyperbolic relationship exists which can be linearized by reciprocal plotting. A corresponding experiment is carried out with blood and dilution of the blood of a normal donor and a correlation coefficient of r = 0.998 obtained.

Example 5

12 Plasmas of healthy donors, as well as of donors who are receiving oral anticoagulation therapy, are applied to test strips produced according to Example 1 and the reaction time determined. The Quick value is determined on the same plasmas with a commercially available Quick reagent (Thromboquant PT). The measurement values of both test systems are correlated with one another by means of linear regression. There is obtained the regression line y = 15.4 + 0.76 × X and a correlation coefficient of r = 0.89.

Example 6

Determination of prothrombin in blood or plasma

Test principle:

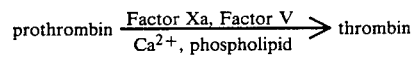

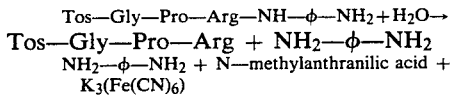

$NH_2-\phi-NH_2$ + N—methylanthranilic acid + $K_3(Fe(CN)_6)$
→ blue colored material FIG. 3 shows the construction of the test strip. In this FIG.3:
1 carrier film
2 and 2a distance blocks
3 application matrix
4 glass fibre fleece (separation fleece)
5 glass fiber fleece (transport fleece)
7 and 11 reagent papers
6 and 10 oxidation papers
7a substrate paper
9 transparent covering film.

The fleece used on the left side of the test strip have a breadth of 0.6 cm. and on the right side are used strips of 1.0 cm. breadth.

Reagent Paper (11)

An impregnation solution of the following end concentration is prepared:

| | |
|---|---|
| Tris-HCl, 50 mmol/l.; pH 8.4; | |
| calcium chloride, 5 mmol/l.; | |
| cephaline, 1 g./l.; | co-factors of the thrombin |
| Factor Xa, 1000 U/l.; | formation |
| Factor V, 100% normal | |

A paper of appropriate thickness and absorbency, for example tea bag paper, is impregnated with this impregnation solution. It is dried at 30° C. and subsequently strips of 1 cm. or 0.6 cm. breadth are cut therefrom.

Oxidation fleece (10)

An impregnation solution of the following composition is prepared:
potassium ferricyanide, 20 mmol/l.;
potassium ferrocyanide, 20 mmol/l.

As described, a paper of appropriate thickness and absorbency is impregnated. It is dried at 30° C. and subsequently strips are produced of 1 cm. or 0.6 cm. breadth.

Substrate Paper (7a)

An impregnation solution is prepared of the following composition:
Tris - HCl, 100 mmol/l., pH 8.1;
N-methylanthranilic acid, 40 mmol/l.;
substrate (Tos—Gly—Pro—Arg—NH—$\phi$—NH$_2$), 1 mmol/l As described, a paper of appropriate thickness and absorbency is impregnated. It is dried at 30° C. and subsequently cut up into strips of 1 cm. breadth.

Carrying out of the prothrombin determination

30 μl. citrate blood or citrate plasma, diluted 6.25 fold, are applied to the application matrix 3. The plasma part of the sample applied then penetrates the oxidation Paper 10 (it has proved to be advantageous to apply this fleece at this place where, reaction-mechanistically, it is per se not needed) and thereafter penetrates the separation fleece 4 and the reagent paper 11. Subsequently, the sample with the dissolved reagent (Factor V, Factor Xa, phospholipid, Ca$^{2+}$) passes into the transport fleece 5 where activation of prothrombin to thrombin by Factor Xa takes place.

After 30 seconds, the transparent covering film 8 and, with it, the underlying fleece (reagent paper 6, oxidation paper 7, substrate paper 7a) is pressed on to the transport fleece 5. Simultaneously, Factor Xa is thereby made available for the activation of residual prothrombin and simultaneously the substrate reaction of active thrombin is initiated.

If these concentration units/30 seconds are plotted against the % prothrombin content of the sample (normal plasma pool) in a dilution series, then a calibration curve is obtained from which can be read off the prothrombin content of an unknown sample (FIG. 4).

Example 7

As described in Example 1, a test strip is produced with the there-given composition but with replacement of the N-methylanthranilic acid as coupling component for the color formation by one of the other compounds set out in the following Table as coupling component. The Table shows the coupling components, the concentration used in the production of the solution with which the reagent and substrate paper is impregnated and the wavelength maximum of the color formed in the case of the reaction with the liberated p-phenylenediamine. For comparison, the corresponding values for N-methylanthranilic acid are also given.

| color-forming coupling component | M.W. | concentration in the solution | maximum in the spectrum |
| --- | --- | --- | --- |
| N-methylanthranilic acid | 151 | 250 mmol/l. | 680 nm |
| EST$^+$ (N-ethyl-N-$\beta$-sulphoethyl-m-toluidine) | 283.32 | 250 mmol/l. | 525 nm |
| ETTS$^{++}$ (N-ethyl-toluidinotoluene-sulphonic acid) | 343 | 250 mmol/l. | 780 nm |
| primaquine diphosphate | 455.35 | 35.1 mmol/l. | 460 nm |
| 2,3-xylenol | 122.17 | 200 mmol/l. | 530 nm |
| diethylmetanilic acid | | 20 mg./ml. | 715 nm |

$^+$EST is also called N-ethyl-3-methyl-N-($\beta$-sulphoethyl)-aniline
$^{++}$ETTS potassium salt Example 8

Test for the determination of the one-phase coagulation time according to Quick (thromboplastin time)

Preparation of the coating mass and of the reagent film 3.2 mg. Tos-Gly-Pro-Arg-p-phenylenediamine, 52 mg. calcium N-methylanthranilate, 150 mg. polybrene, 300 mg. rabbit brain thromboplastin and 10 mg. Ficoll are incorporated into 10 ml. of a 1.5% solution of hydroxypropyl cellulose in 0.02 M Hepes buffer (pH 7.8). The so prepared coating mass is coated with a wet film thickness of 150μ on to a transparent film and dried at 35° C.

Production of the oxidation matrix

A nylon mesh with a filament thickness of 30μ and a filament count of 185 filaments/cm. is impregnated with a 0.015 molar solution of potassium ferricyanide and dried at 50° C.

The reagent and substrate paper are worked up to a test strip according to FIG. 1, only the reagent substrate paper 7 thereby lying fixedly on the transparent covering film 8.

If, as described in Example 1, citrate blood is applied, followed by proceeding as there described, then, in the case of reference to the time which is needed for a remission decrease of 2%, there are obtained, as measurement variable, the following measurement values:

| % Quick | seconds up to a decrease of 2% of the remission |
| --- | --- |
| 100% | 51.5 |
| 50% | 56.4 |
| 35% | 64.3 |
| 25% | 75.0 |
| 12.4% | 107 |
| 10% | 121 |

We claim:
1. Test strip useful in carrying out a Quick Test, a partial prothromboplastin time test, or in an analysis of one of prothrombin, Factor VII, Factor VIII, Factor IX and Factor X, comprising:
(i) a carrier material containing (ii) a protease which reacts with prothrombin, Factor VII, Factor VIII, Factor IX or Factor X to yield an activated protease; (iii) a chromophoric protease substrate cleavable by said activated protease in a reaction which does not change the course of the intrinsic or extrinsic coagulation cascade system of blood in the presence of said carrier material, (iv) a buffer, and (v) at least one additional member of the intrinsic or extrinsic coagulation cascade system, wherein said protease reacts with prothrombin, Factor VII, Factor VIII, Factor IX or Factor X in a reaction which is part of the intrinsic or extrinsic coagulation cascade system wherein (ii), (v) are dried on said carrier material.

2. The test strip of claim 1 further comprising a second carrier material comprising an oxidizing agent, and said first carrier material further comprises an aniline or phenol derivative which forms a colored compound with the chromophoric protease substrate after said chromophoric protease substrate has been cleaved by said protease to release a chromophore in the presence of said oxidizing agent.

3. The test strip of claim 2 wherein the aniline or phenol derivative is N-methylanthranilic acid, dimethylanthranilic acid, N-ethyl-N-(3'-sulphobenzene)-aniline or 2,3- xylenol.

4. The test strip of claim 2, wherein said chromophoric substrate is Tos-Gly-Pro-Arg-p-phenylenediamine, said aniline derivative is N-methylanthranilic acid and said oxidizing agent is potassium ferricyanide.

5. The test strip of claim 2, further comprising a third sample receiving carrier material positioned above or below said first carrier material.

6. The test strip of claim 5, further comprising a fiber fleece arranged between the third and first carrier material and separating said third and first carrier materials from each other.

7. The test strip of claim 5, further comprising a fiber fleece arranged between the first and second carrier material and separating said first and second carrier materials from each other.

8. The test strip of claim 1 useful in carrying out a Quick Test, comprising thromboplastin, a chromophoric substrate for thrombin and $Ca^{2+}$ ions.

9. The test strip of claim 1 useful in analysis of prothrombin, comprising Factor X$a$, Factor V, $Ca^{2+}$ ions and a phospholipid.

10. The test strip of claim 1 useful in carrying out a partial thromboplastin time test, comprising a thrombin activator, a contact factor activator, a chromophoric substrate for thrombin, and $Ca^{2+}$ ions.

11. The test strip of claim 10, further comprising ellagic acid and a phospholipid.

12. The test strip of claim 1 useful in analysis of Factor X, comprising at least one factor involved in blood coagulation selected from the group consisting of venom obtained from Russell's viper and Factor X activating enzyme derived from Russell's viper venom, and further comprising $Ca^{2+}$ ions and a chromophoric substrate for factor X$a$.

13. The test strip of claim 1 useful in analysis of Factor VIII, comprising Factor IX$a$, thrombin, $Ca^{2+}$ ions, a phospholipid and one member of the group consisting of a chromophoric substrate for Factor X$a$ and a chromophoric substrate for thrombin.

14. The test strip of claim 1 useful in analysis of Factor VII, comprising thromboplastin, $Ca^{2+}$ ions and a chromophoric substrate for Factor X$a$.

15. The test strip of claim 1 useful in analysis of factor IX comprising an activated contact factor, Factor IX$a$, $Ca^{2+}$ ions and one of a chromophoric substrate for Factor IX$a$, or a combination of phospholipid, Factor VIII, thrombin and a chromophoric substrate for Factor X$a$.

16. The test strip of claim 1 wherein said chromphoric substrate is a compound of the formula

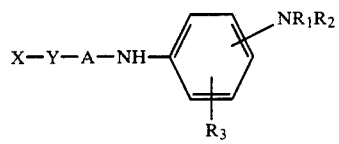

wherein A is the amino acid arginine or lysine, X is an N-terminal amino acid protective group, Y is a single bond or a chain of 1 to 3 amino acids, $NR_1R_2$ is a group in the o- or p-position in which $R_1$ and $R_2$, independently of one another, are hydrogen, alkyl containing up to 3 carbon atoms or nitro and $R_3$ is hydrogen, a carboxyl ester or carboxylamido group, halogen, nitro or an alkyl containing up to 3 carbon atoms.

17. The test strip of claim 16 wherein said chromophoric substrate is a Tos-Gly-Pro-Arg derivative.

18. The test strip of claim 16, further comprising a second carrier material which comprises an oxidizing agent and said first carrier material comprises an aniline or phenol derivative which forms a colored compound with the chromophore of the chromophoric substrate in the presence of said oxidizing agent.

19. The test strip of claim 1, wherein the carrier material is absorbent.

* * * * *

UNITED STATES PATENT AND TRADEMARK OFFICE
CERTIFICATE OF CORRECTION

PATENT NO. : 5,059,525
DATED : October 22, 1991
INVENTOR(S) : Knut Bartl et al.

It is certified that error appears in the above-identified patent and that said Letters Patent is hereby corrected as shown below:

Column 3, line 56 should be changed from "methylhydroxyethyl celluloses, hydroxyethylmethyl celluloses ..." to -- methylhydroxyethyl celluloses, hydroxyethyl celluloses, hydroxypropyl celluloses and hydroxypropylmethyl celluloses...--.

Column 5, line 10: change "2 and 3a distance block" to -- 2 and 2a distance block --.

Column 5, line 21: after "film", "," should be -- 8 --.

Column 6, line 52: change "9 transparent covering film" to -- 8 transparent covering film --.

Signed and Sealed this

Thirty-first Day of August, 1993

*Attest:*

BRUCE LEHMAN

*Attesting Officer*     Commissioner of Patents and Trademarks